(12) United States Patent
Kim et al.

(10) Patent No.: US 11,376,148 B2
(45) Date of Patent: Jul. 5, 2022

(54) COMBINED STRUCTURE OF WEARABLE APPARATUS

(71) Applicants: Hyundai Motor Company, Seoul (KR); Kia Motors Corporation, Seoul (KR)

(72) Inventors: Kyu Jung Kim, Seoul (KP); Hyun Seop Lim, Gyeonggi-do (KR); Beom Su Kim, Gyeonggi-do (KR); Dong Jin Hyun, Gyeonggi-do (KR); Ki Hyeon Bae, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 16/691,362

(22) Filed: Nov. 21, 2019

(65) Prior Publication Data

US 2020/0315830 A1 Oct. 8, 2020

(30) Foreign Application Priority Data

Apr. 4, 2019 (KR) .......................... 10-2019-0039702

(51) Int. Cl.
*A61F 5/01* (2006.01)

(52) U.S. Cl.
CPC .................................... *A61F 5/013* (2013.01)

(58) Field of Classification Search
CPC ...... A61F 5/013; A61F 5/0118; A61F 5/3723; A61F 5/05858; A61F 5/0102; A61F 5/00; A61F 5/01; A61F 5/058; A61F 5/05841; A61F 5/026; A61F 5/02; A61F 5/04; A61F 2005/0132; A61F 2005/0144; A61F 2005/0146; B25J 9/0006; G06F 3/013; A61H 2201/165; A61H 1/00; A61H 1/0218; A61H 3/00; A61H 3/008

(Continued)

(56) References Cited

U.S. PATENT DOCUMENTS 6,082,034 A    7/2000  Musmanno
9,652,037 B2 * 5/2017  Rubin ..................... A63F 13/24
(Continued)

FOREIGN PATENT DOCUMENTS

JP    2014113666 A  *  6/2014  ............. B25J 11/00
KR  20160071661 A  *  6/2016  ................ B25J 9/00
(Continued)

*Primary Examiner* — Caitlin A Carreiro
(74) *Attorney, Agent, or Firm* — Fox Rothschild LLP

(57) ABSTRACT

A combined structure of a wearable apparatus includes: a torso fastening part fixedly fastened to a wearer's torso; a fixed link extending from the torso fastening part to a position above a wearer's shoulder; a first link and a second link being respectively coupled to the fixed link to be laterally rotatable, and crossing each other while being vertically spaced apart from each other; a rotatable part disposed at a position above the wearer's shoulder, and coupled to the first link and the second link to be laterally rotatable; a connecting part coupled to the rotatable part; and an upper arm module coupled to be rotatable upward or downward about the connecting part while an end thereof is coupled to the connecting part at a position corresponding to an upper end portion of a wearer's upper arm.

12 Claims, 13 Drawing Sheets

(58) Field of Classification Search
USPC ..... 601/33, 1, 23; 602/5, 16, 20, 23, 19, 21,
602/32; 128/845
See application file for complete search history.

(56) References Cited

U.S. PATENT DOCUMENTS

| | | | |
|---|---|---|---|
| 10,058,994 B2 * | 8/2018 | Angold | .................. B25J 9/0006 |
| 2004/0083932 A1 * | 5/2004 | Kottman | .................. A47B 3/00 |
| | | | 108/115 |
| 2010/0114329 A1 * | 5/2010 | Casler | .................. B62D 57/032 |
| | | | 623/24 |
| 2011/0164949 A1 | 7/2011 | Kim et al. | |
| 2016/0081871 A1 | 3/2016 | Doyle | |

FOREIGN PATENT DOCUMENTS

| | | | | |
|---|---|---|---|---|
| KR | 10-2016-0132156 A | 11/2016 | | |
| KR | 10-1896181 B1 | 9/2018 | | |
| KR | 20180136940 A * | 12/2018 | ............ | B25J 9/0006 |
| WO | 2018/082906 A1 | 5/2018 | | |

* cited by examiner ered longitudinal axis thereof.

COMBINED STRUCTURE OF WEARABLE APPARATUS

CROSS REFERENCE TO RELATED APPLICATION

The present application claims under 35 U.S.C. § 119(a) the benefit of Korean Patent Application No. 10-2019-0039702, filed Apr. 4, 2019, the entire contents of which are incorporated by reference herein.

BACKGROUND

(a) Technical Field

The present disclosure relates generally to a combined structure of a wearable apparatus, more particularly, to a structure configured to be combined with a wearer to simulate the rotation of a wearer's shoulder joint through a cross four-bar linkage.

(b) Description of the Related Art

A wearable robot is a robot that assists movement of a wearer's body by putting the robot on a specific part of the body or by mounting the robot to a specific part, and is designed to be used for medical, military, or industrial purposes. In particular, in the case of wearable robots for the workplace, such wearable robots are designed to prevent injuries and to support muscle strength by reducing a load applied to the wearer. The wearable robot is one made by mimicking a wearer's exoskeleton, and it is important to design a joint to have the same motion as the actual motion of the body.

In particular, a wearable muscular strength assisting apparatus includes a manual support mechanism configured to support a person supporting the weight of a tool. A typical manual support mechanism is configured to compensate for gravity under a range of positions by using a combination of structural elements, springs, cables, and pulleys. The configuration of these devices provides gravity compensation within a limited operating range of operation.

However, the conventional wearable apparatus is problematic in that it is impossible to simulate the lateral rotation of a wearer's shoulder joint. In particular, when a wearer performs internal rotation or external rotation of his or her shoulder joint, a center of rotation is moved instead of being a fixed center of rotation. As a result, when an upper arm assisting apparatus is configured to be rotatable about a single rotation shaft in the up-and-down direction, it is impossible to simulate the rotational motion of the shoulder joint.

Further, to solve the above problem, when a plurality of rotation shafts in the up-and-down direction is provided, an extra degree of freedom occurs, so additional coupling to the wearer is required, and during the external rotation of the shoulder joint, the rotation shafts and the components thereof may be projected to the outside, which may cause a great risk of accident.

The foregoing is intended merely to aid in the understanding of the background of the present disclosure, and is not intended to mean that the present disclosure falls within the purview of the related art that is already known to those skilled in the art.

SUMMARY

Accordingly, the present disclosure proposes a combined structure of a wearable apparatus, in which it is possible to stably simulate internal rotation or external rotation of a wearer's shoulder joint with a single degree of freedom.

In order to achieve the above object, according to one aspect of the present disclosure, there is provided a combined structure of a wearable apparatus, the combined structure including: a torso fastening part fixedly fastened to a wearer's torso; a fixed link extending from the torso fastening part to a position above a wearer's shoulder; a first link and a second link being respectively coupled to the fixed link to be laterally rotatable, and crossing each other while being vertically spaced apart from each other; a rotatable part disposed at a position above the wearer's shoulder, and coupled to the first link and the second link to be laterally rotatable; a connecting part coupled to the rotatable part to extend downward from the rotatable part; and an upper arm module coupled to be rotatable upward or downward about the connecting part while an end thereof is coupled to the connecting part at a position corresponding to an upper end portion of the wearer's upper arm, and fastened to the wearer's upper arm while extending in a longitudinal direction of the wearer's upper arm.

The torso fastening part may be disposed at a wearer's back side, and may include: an upper plate disposed at an upper portion of the torso fastening part to be brought in contact with the wearer's back side; a lower plate disposed at a lower portion of the torso fastening part to be brought in contact with the wearer's back side; and a rear side link extending in a vertical direction to connect the upper plate and the lower plate together.

The rear side link may be rotatably coupled to the upper plate or the lower plate about an extended longitudinal direction thereof as a rotation axis.

The upper plate may be fastened to the wearer's back side at a position higher than the wearer's shoulder, and the fixed link may be disposed at a position above the wearer's shoulder by extending forward from a position where the upper plate is laterally extended.

The lower plate may be fastened to the wearer's back side at a position corresponding to a wearer's pelvis, and the lower plate may be coupled to the rear side link to be rotatable forward or backward.

The lower plate may be provided with a first coupling portion and a second coupling portion protrudingly extending from positions vertically spaced apart from each other, and the rear side link may be coupled to the first coupling portion and the second coupling portion, wherein the first coupling portion is rotatably coupled to the rear side link, and the second coupling portion is slidably coupled to the rear side link.

The fixed link may extend forward from the torso fastening part to be disposed at a position above the wearer's shoulder, and may be rotatably coupled to the first link and the second link respectively at a first point and a second point spaced apart from each other.

The rotatable part may be in the form of a plate extending parallel to the ground, may be rotatably coupled to the first link and the second link respectively at a third point and a fourth point spaced apart from each other, and may be coupled to the connecting part at a fifth point spaced apart from the third point and the fourth point.

The upper arm module may be applied with a rotational torque that rotates the upper arm module upwardly with respect to the connecting part, and the fifth point of the rotatable part coupled with the connecting part may be disposed at a position behind an intersection of the first link and the second link.

The first link or the second link may be coupled to the fixed link or the rotatable part through a thrust bearing, and may extend on planes parallel to each other while being vertically spaced from each other.

The combined structure may further include: a first magnetic body disposed at an end of the rotatable part spaced apart from positions where the rotatable part is coupled to the first link and the second link; and a second magnetic body disposed at a lateral end of the torso fastening part, wherein the first magnetic body and second magnetic body are attracted to each other.

The upper arm module may be disposed at an outer side of a wearer's upper arm, and may include a support that supports the wearer's upper arm from a lower portion of the wearer's upper arm by extending toward an inner side of the wearer's upper arm through the lower portion of the wearer's upper arm.

According to the combined structure of a wearable apparatus of the present disclosure, it is possible to exactly simulate a center of rotation that has moved according to internal rotation or external rotation of the wearer's shoulder joint, thereby allowing motion to be implemented without any discomfort.

Further, without requiring an additional fastening mechanism to a wearer's body or configuration protruding by being spaced apart from the wearer's body, motion is implemented with a single degree of freedom, so it is possible to improve stability.

BRIEF DESCRIPTION OF THE DRAWINGS

The above and other objects, features and other advantages of the present disclosure will be more clearly understood from the following detailed description when taken in conjunction with the accompanying drawings, in which.

DETAILED DESCRIPTION OF THE DISCLOSURE

Figure 1:
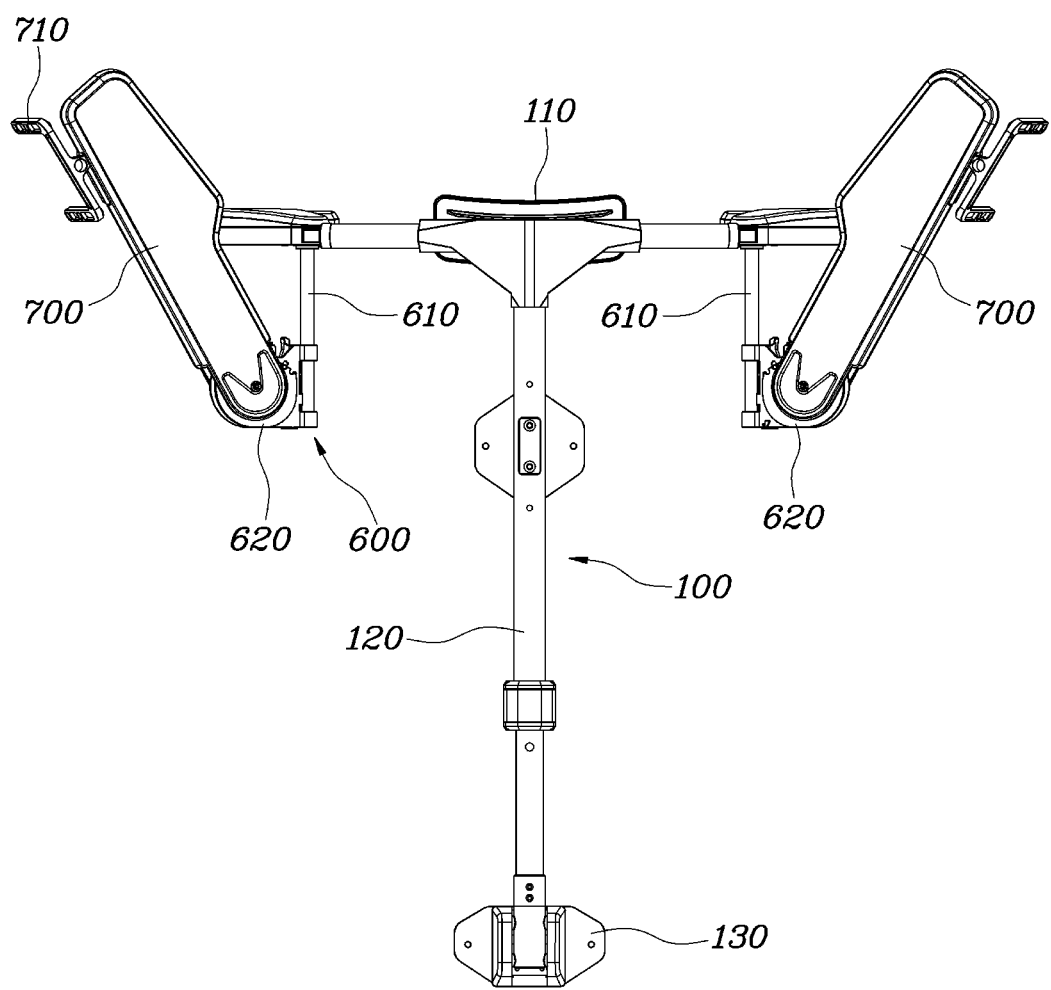
FIG. 1 is a rear view showing a combined structure of a wearable apparatus according to an embodiment of the present disclosure.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

In the following description, the structural or functional description specified to exemplary embodiments according to the concept of the present disclosure is intended to describe the exemplary embodiments, so it should be understood that the present disclosure may be variously embodied, without being limited to the exemplary embodiments.

The exemplary embodiments according to the concept of the present disclosure may be variously modified and may have various shapes, so examples of which are illustrated in the accompanying drawings and will be described in detail with reference to the accompanying drawings. However, it should be understood that the exemplary embodiments according to the concept of the present disclosure are not limited to the embodiments which will be described hereinbelow with reference to the accompanying drawings, but various modifications, equivalents, additions and substitutions are possible, without departing from the scope and spirit of the disclosure.

It will be understood that, although the terms first, second, etc. may be used herein to describe various elements, these elements should not be limited by these terms. These terms are only used to distinguish one element, from another element. For instance, a first element discussed below could be termed a second element without departing from the teachings of the present disclosure. Similarly, the second element could also be termed the first element.

It will be understood that when an element is referral to as being "coupled" or "connected" to another element, it can be directly coupled or connected to the other element or intervening elements may be present therebetween. In contrast, it should be understood that when an element is referred to as being "directly coupled" or "directly connected" to another element, there are no intervening elements present. Further, the terms used herein to describe a relationship between elements, for example, "between", "directly between", "adjacent" or "directly adjacent" should be interpreted in the same manner as those described above. Unless otherwise defined, all terms including technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, an exemplary embodiment of the present disclosure will be described in detail with reference to the accompanying drawings. Throughout the drawings, the same reference numerals will refer to the same or like parts.

Figure 2:
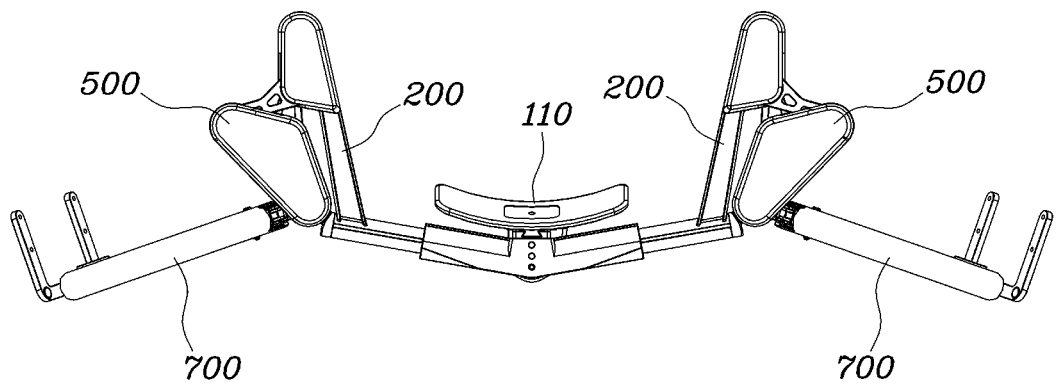
FIG. 2 is a top view showing the combined structure of a wearable apparatus according to an embodiment of the present disclosure.

FIG. 1 is a rear view showing a combined structure of a wearable apparatus according to an embodiment of the present disclosure; and FIG. 2 is a top view showing the combined structure of a wearable apparatus according to an embodiment of the present disclosure.

With reference to FIGS. 1 and 2, a combined structure of a wearable apparatus according to an embodiment of the present disclosure includes: a torso fastening part 100 fixedly fastened to a wearer's torso; a fixed link 200 extending from the torso fastening part 100 to a position above a wearer's shoulder; a first link 300 and a second link 400 being respectively coupled to the fixed link 200 to be laterally rotatable, and crossing each other while being vertically spaced apart from each other; a rotatable part 500 disposed at a position above the wearer's shoulder, and coupled to the first link 300 and the second link 400 to be laterally rotatable; a connecting part 600 coupled to the rotatable part 500 to extend downward from the rotatable part 500; and an upper arm module 700 coupled to be rotatable upward or downward about the connecting part 600 while an end thereof is coupled to the connecting part 600 at a position corresponding to an upper end portion of a wearer's upper arm, and fastened to the wearer's upper arm while extending in a longitudinal direction of the wearer's upper arm.

The torso fastening part 100, which is fastened to the wearer's torso, may be secured to the wearer's torso via a separate harness or the like.

The fixed link 200 may be fixedly coupled to the torso fastening part 100 and extend toward the position above the wearer's shoulder. In particular, the fixed link may extend from the torso fastening part 100 to respective opposite sides of the shoulder of the wearer.

The rotatable part 500 may be rotatably coupled to the fixed link 200 through the first link 300 and the second link 400. In particular, the first link 300 and the second link 400 are coupled to the rotatable part 500 and the fixed link 200 respectively so as to be laterally rotatable, and thus, both the fixed link 200 and the rotatable part 500 may be rotatably coupled to each other in a direction parallel to the ground.

The first link 300 and second link 400 may be respectively coupled to the rotatable part 500 and fixed link 200 to form a four-bar linkage structure. In particular, the first link 300 and the second link 400 may be arranged so as to be spaced apart from each other in the vertical direction and cross each other while being extended on planes parallel to each other.

The first link 300 and the second link 400 may be laterally rotatable about the fixed link 200 fixed to the wearer's torso, and the rotatable part 500 coupled to the first link 300 and the second link 400 to be laterally rotatable is rotated about an instantaneous center of rotation (ICR) 540 formed at the intersection of the first link 300 and the second link 400.

In other words, the rotatable part 500 is rotated about the ICR 540 moved according to rotations of the first link 300 and the second link 400, so that the end of the rotatable part 500 can be rotated to simulate the movement of the end of the wearer's shoulder joint.

The upper arm module 700 may be coupled to the connecting part 600 to be rotatable upward or downward about an end of the upper arm module. In particular, the connecting part 600 may include: a first connecting part 610 extending downward from one point of the rotatable part 500; and a second connecting part 620 extending from the first connecting part 610 to a position corresponding to the upper end portion of the wearer's upper arm along the direction parallel to the ground.

The first connecting part 610 may be disposed at the wearer's back side, and the second connecting part 620 may extend from the wearer's back side to the wearer's outer side. The end of the upper arm module 700 may be coupled to the second connecting part 620 at the wearer's outer side to be rotatable about a position that matches the center of rotation of the wearer's upper arm.

As another embodiment, the first connecting part 610 and the second connecting part 620 may be integrally formed into one configuration, and directly connect the rotatable part 500 and the upper arm module 700 together.

Accordingly, as the rotatable part is connected to the crossed first link 300 and second link 400, it is possible to naturally simulate the movement of the end of the wearer's shoulder joint.

In particular, the upper arm module 700 may extend in the extension direction of the wearer's upper arm, and may generate rotational torque that rotates the wearer's upper arm upward or downward. A torso support can support a reaction against this rotational torque in the torso.

The upper arm module 700 may be provided therein with an elastic body such as a spring generating an elastic force, wherein the elastic body is connected to a wire wound or unwound according to an angle at which the upper arm module 700 is rotated upward or downward about one end thereof, whereby the elastic force of the elastic body can be varied according to the rotation angle of the upper arm module 700.

Further, the rotational torque is varied according to the magnitude of the elastic force and the direction where the elastic force is applied, and a profile of the rotational torque according to the rotation angle of the upper arm module 700 may be designed by providing a cam in the upper arm module 700, which induces the wire to be wound or the elastic body to be deformed according to the rotation angle of the upper arm module 700.

The upper arm module 700 may be disposed at an outer side of the wearer's upper arm, and the upper arm module 700 may include a support 710 that supports the wearer's upper arm from a lower portion of the wearer's upper arm by extending to an inner side of the wearer's upper arm through the lower portion of the wearer's upper arm. The support 710 may be in a shape that surrounds the lower portion of the wearer's upper arm.

Figure 3:
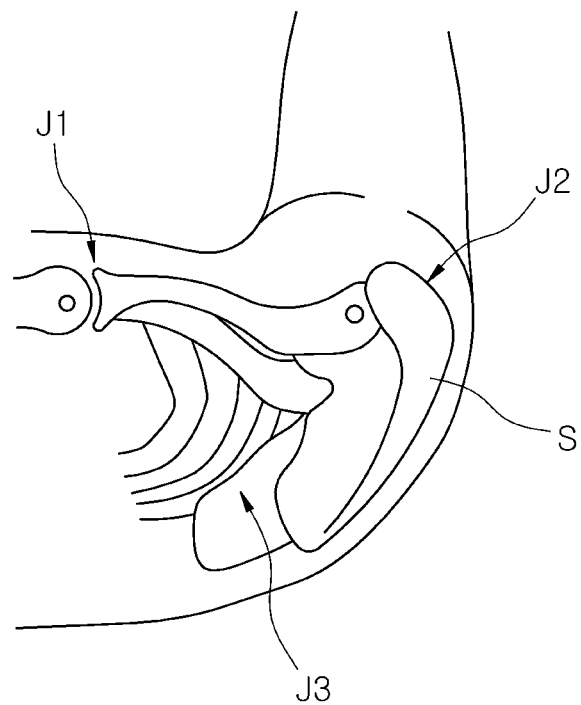
FIGS. 3 and 4 are views showing joints constituting a shoulder of a human body and movements according to rotation.
Figure 4:
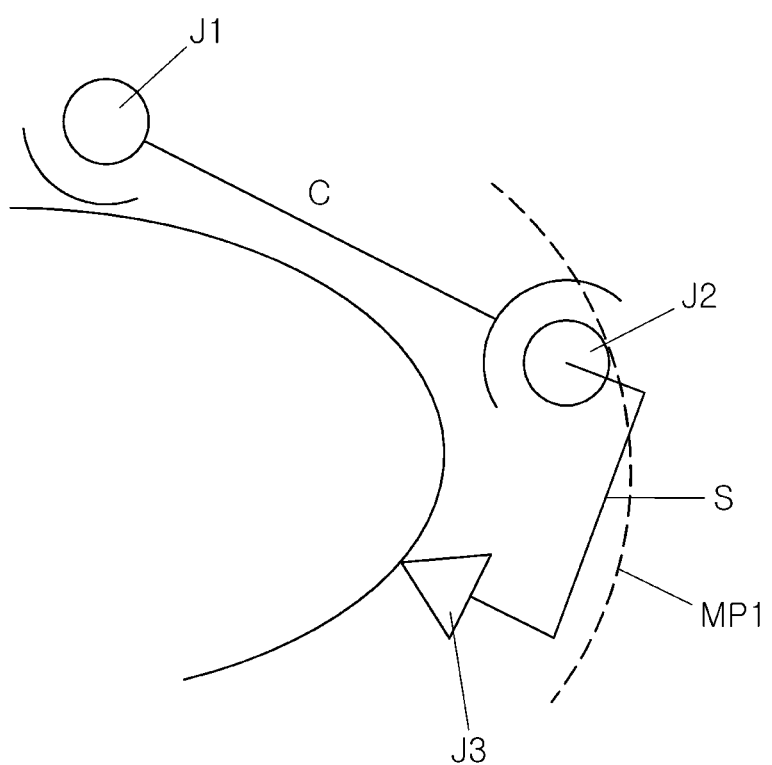

FIGS. 3 and 4 are views showing joints constituting a shoulder of a human body and movements according to rotation.

With reference to FIGS. 3 and 4, the shoulder of the human body is composed of complex joints J1, J2, and J3, and rotations thereof are combined to realize the upward and downward movements of the scapula S, and upward and downward rotation of the shoulder including internal rotation and external rotation.

In particular, the shoulder joint consists of a sterno-clavicular joint J1, an acromio-clavicular joint J2, and a scapulo-thoracic joint J3 connected to each other on a horizontal plane. When the shoulder joint rotates internally or externally on the horizontal plane, the sterno-clavicular joint J1 and the acromio-clavicular joint J2 simultaneously rotate, and thus, a complex rotation occurs in which the scapula S and the clavicle C rotate. Accordingly, the wearer's upper arm moves while the center of rotation MP1 thereof is changed. This rotational motion cannot be simulated with a single rotation axis, as described below.

Figure 5:
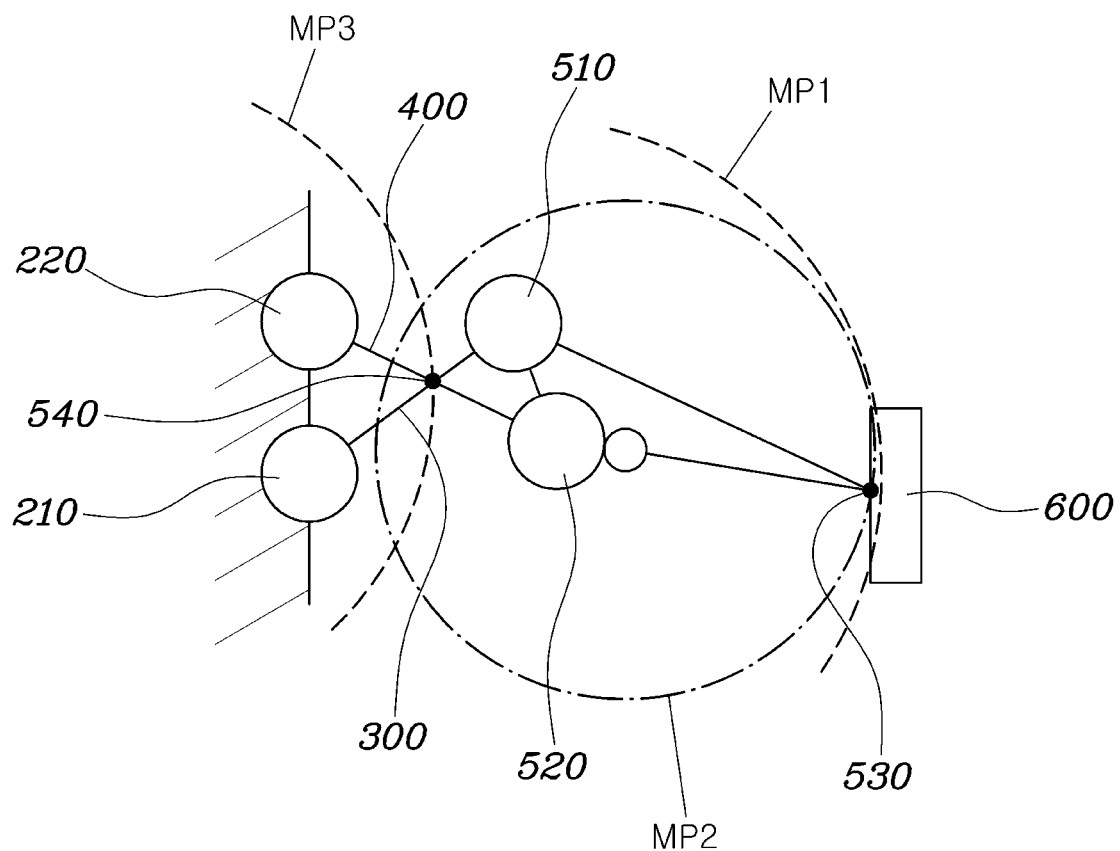
FIG. 5 is a view comparing a moving path of rotation according to the combined structure of a wearable apparatus according to an embodiment of the present disclosure with a moving path of rotation according to a single axis.

FIG. 5 is a view comparing a moving path of rotation MP1 according to the combined structure of a wearable apparatus according to an embodiment of the present disclosure with a moving path of rotation according to a single axis MP2.

With further reference to FIG. 5, the combined structure of a wearable apparatus according to an embodiment of the present disclosure has a four-bar linkage structure in which the first link 300 and the second link 400 cross each other, so the ICR 540 is rotated as the first link 300 and the second link 400 are laterally rotated, whereby an end (a fifth point 530 to be described below) of the rotatable part 500 can be moved to simulate the movement of the center of rotation MP1 of the upper arm that is the end of the wearer's shoulder.

In particular, compared to a path moving along a circumference based on a single rotation axis MP2, the end of the rotatable part of the rotatable part can be moved to exactly simulate the movement of the center of rotation MP1 of the upper arm that is the end of the wearer's shoulder. As a result, it is possible to exactly simulate the movement of the wearer, so that motion without any discomfort is possible.

Figure 6:
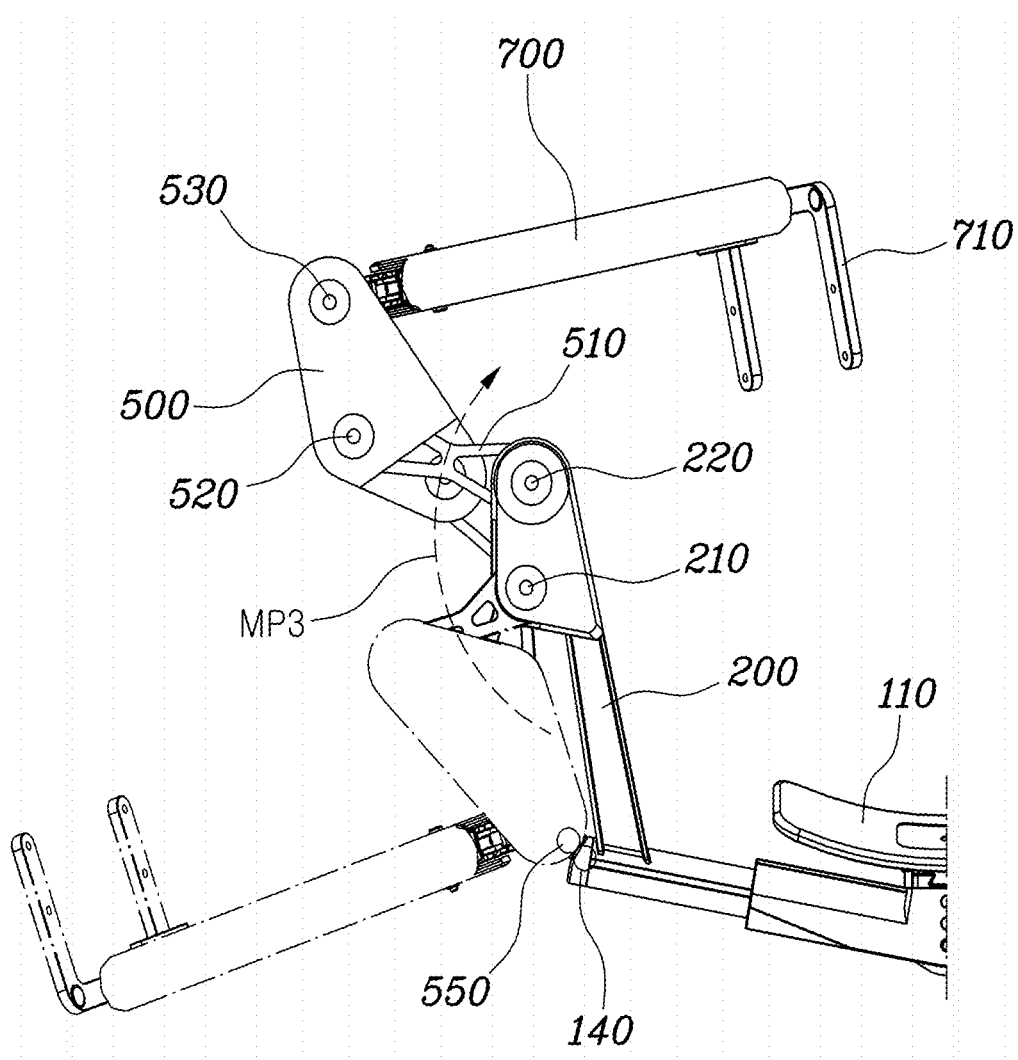
FIG. 6 is a view showing a moving process of the combined structure of a wearable apparatus according to an embodiment of the present disclosure according to internal rotation of a shoulder joint.
Figure 7A:
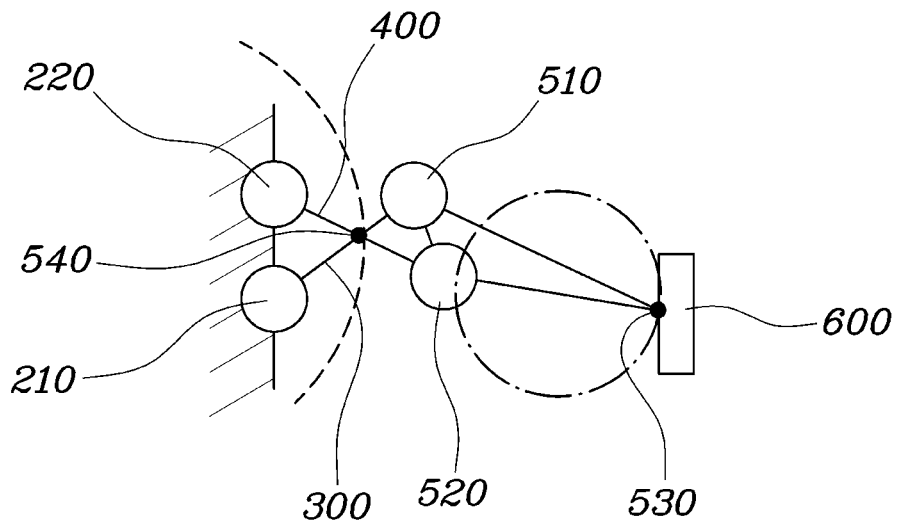
FIGS. 7A, 7B, and 7C are schematic views showing a moving process of the combined structure of a wearable apparatus according to an embodiment of the present disclosure according to internal rotation of a shoulder joint.
Figure 7B:
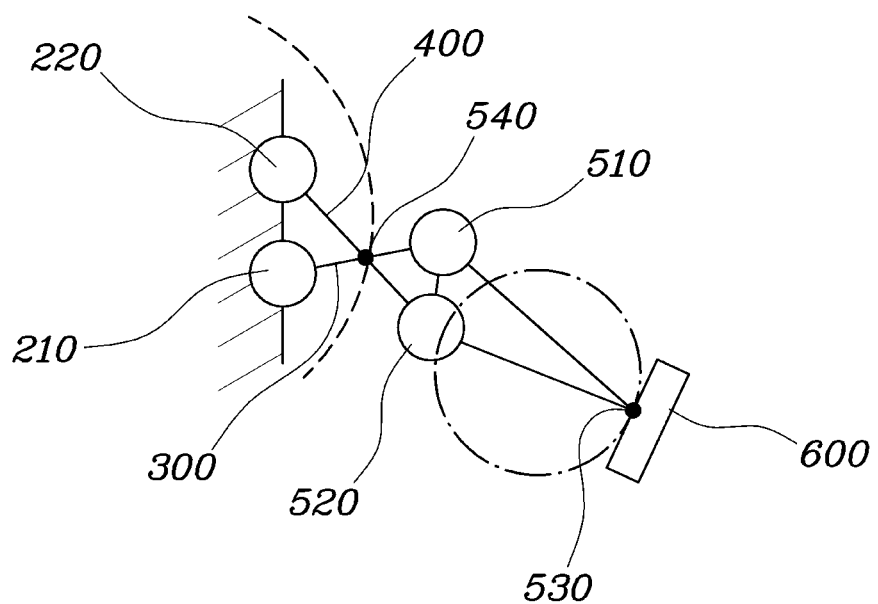
Figure 7C:
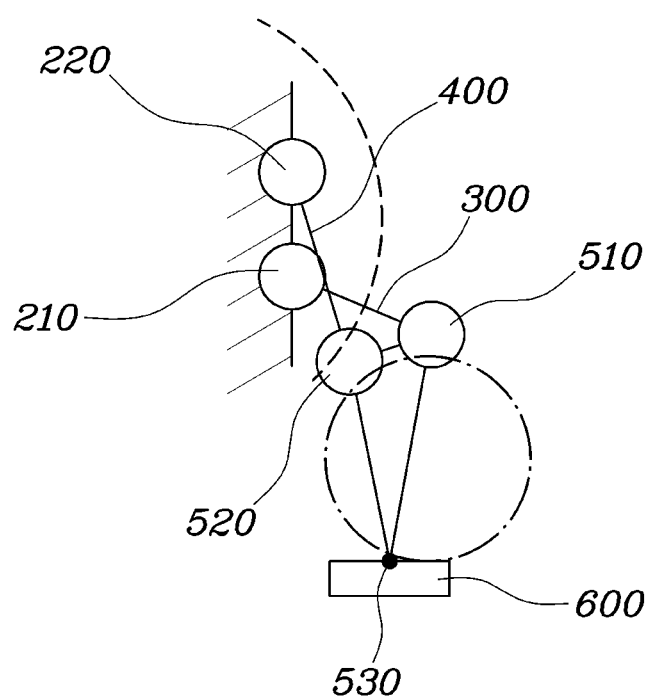
Figure 8:
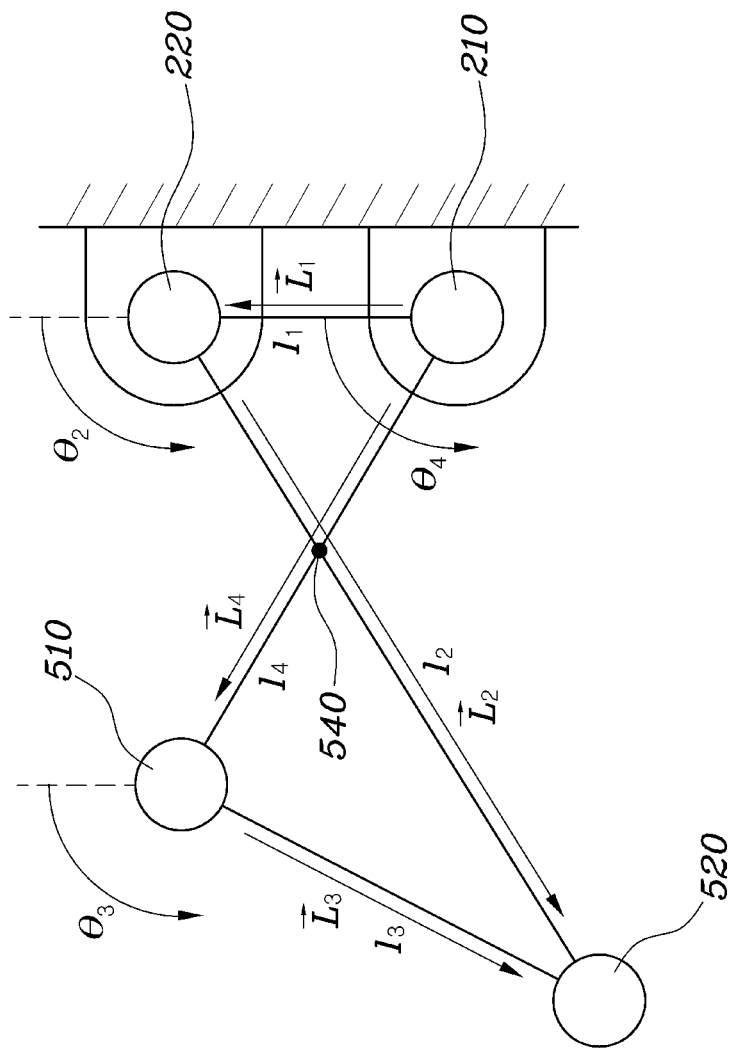
FIGS. 8 and 9 are views showing movements of a first link and a second link included in the combined structure of a wearable apparatus according to an embodiment of the present disclosure.
Figure 9:
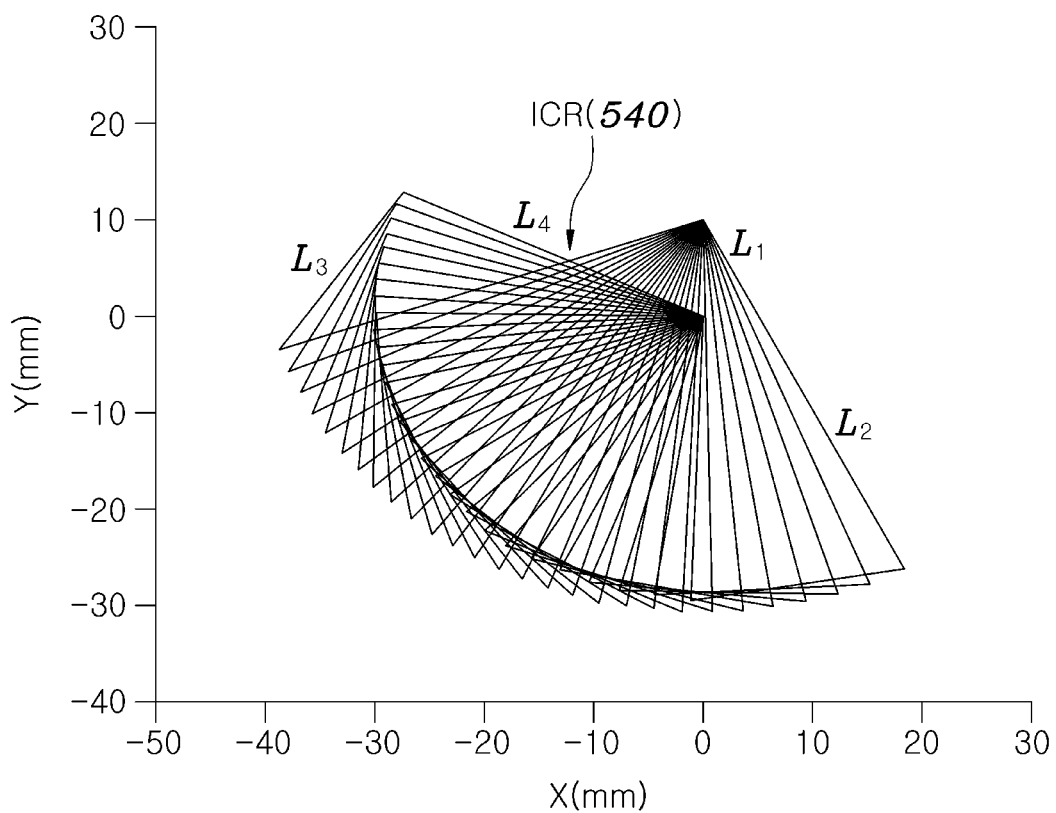
Figure 10:
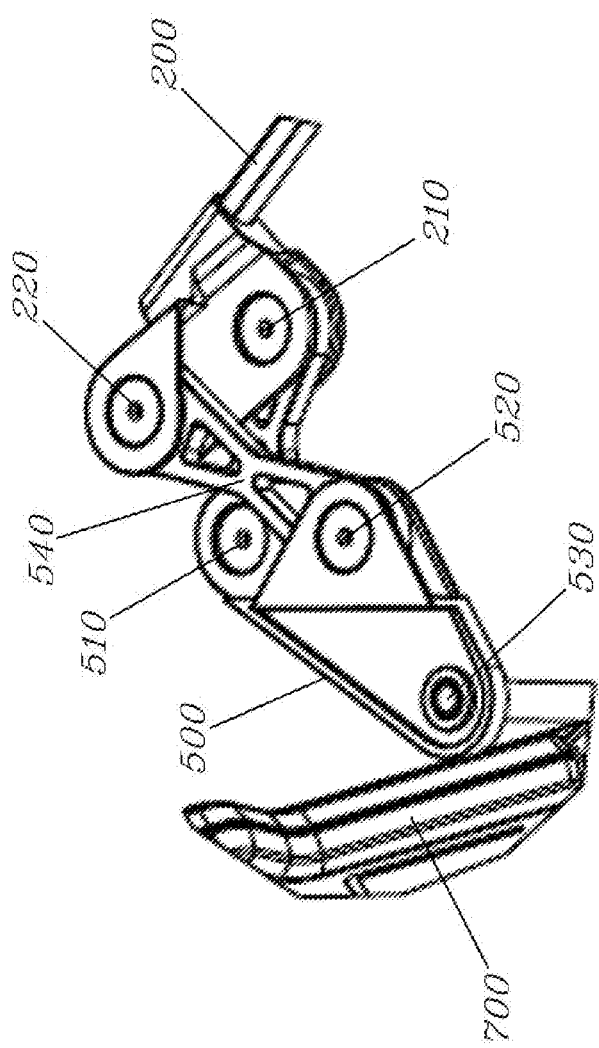
FIG. 10 is an enlarged view showing the first link and the second link included in the combined structure of a wearable apparatus according to an embodiment of the present disclosure.

FIG. 6 is a view showing a moving process of the combined structure of a wearable apparatus according to an embodiment of the present disclosure according to internal rotation of a shoulder joint, depicting a moving path MP3 of the instantaneous center of rotation (ICR) 540; FIGS. 7A, 7B, and 7C are schematic views showing a moving process of the combined structure of a wearable apparatus according to an embodiment of the present disclosure according to internal rotation of a shoulder joint; FIGS. 8 and 9 are views showing movements of a first link and a second link included in the combined structure of a wearable apparatus according to an embodiment of the present disclosure; and FIG. 10 is an enlarged view showing the first link and the second link included in the combined structure of a wearable apparatus according to an embodiment of the present disclosure.

With further reference to FIGS. 6 to 10, the fixed link 200 may extend forward from the torso fastening part 100 to be disposed at a position above the wearer's shoulder, and may be rotatably coupled to the first link 300 and the second link 400 respectively at a first point 210 and a second point 220 spaced apart from each other.

The fixed link 200 may be disposed at a position above the wearer's shoulder by extending forward from the torso fastening part 100 fastened to the wearer's back side. In particular, the first point 210 and the second point 220 of the fixed link 200 may be spaced apart from each other in the forward and backward direction, and may be coupled to the first link 300 at the first point 210 and with the second link 400 at the second point 220.

The first link 300 and second link 400 may extend outwardly from the fixed link 200, and the rotatable part 500 may be coupled to the first link 300 and the second link 400 while being positioned outside the fixed link 200.

Further, the rotatable part 500 may be in the form of a plate extending parallel to the ground, be rotatably coupled to the first link 300 and the second link 400 respectively at a third point 510 and a fourth point 520 spaced apart from each other, and be coupled to the connecting part 600 at a fifth point 530 spaced apart from the third point 510 and the fourth point 520.

The rotatable part 500 may extend in the direction parallel to the ground to be coupled to the first link 300 and the second link 400 at the third point 510 and the fourth point 520 spaced apart from each other in the forward and backward direction. Thus, the first link 300 and the second link 400 may be coupled to each other while extending in the direction parallel to the ground to cross each other between ends thereof.

In particular, the first link 300 and the second link 400 are vertically spaced from each other, wherein the first link 300 may be coupled to a position under the fixed link 200 and the rotatable part 500, and the second link 400 may be coupled to a position above the fixed link 200 and the rotatable part 500, and the reverse is also possible. Thus, the first link 300 and the second link 400 may cross each other without interference.

The fifth point 530 may be spaced apart from the third point 510 and the fourth point 520 of the rotatable part 500, and may be an outer end of the rotatable part 500. In other words, the fifth point 530 may be outer laterally disposed to form a triangle along with the third point 510 and the fourth point 520, and the rotatable part 500 may be a triangular shape having the third point 510, the fourth point 520, and the fifth point 530 as corners.

Thus, the rotatable part 500 rotatably coupled to the first link 300 and the second link 400 is laterally moved by the first link 300 and the second link 400 rotating as a cross four-bar linkage, and accordingly, the fifth point 530 of the rotatable part 500 is capable of rotational movement in which the center of rotation is moved instead of the fixed center of rotation.

The connecting part 600 may be coupled to the rotatable part 500 at the fifth point 530. In particular, the connecting part may be coupled to the first connecting part 610 extending downwardly from the fifth point 530. In particular, the fifth point 530 and the first connecting part 610 may be disposed at a position behind the wearer's shoulder.

The second connecting part 620 may extend to a position corresponding to the upper end portion of the wearer's upper arm along the direction parallel to the ground by being coupled to the first connecting part 610. In particular, the rotatable part 500 and the first connecting part 610, and the first connecting part 610 and the second connecting part 620 may be coupled so that the lateral rotation is restrained. Thus, in order to simulate the external rotation or internal rotation of the wearer's shoulder, compared to the conventional case where the rotatable part 500 and the first connecting part 610, and the first connecting part 610 and the second connecting part 620 are rotatably coupled to form an excessive degree of freedom, according to the present disclosure, it is possible to exactly simulate the movement of the end of the wearer's shoulder using a cross four-bar linkage.

In particular, as shown in FIG. 6, the combined structure of a wearable apparatus may further include: a first magnetic body 550 disposed at an end of the rotatable part 500 spaced apart from positions where the rotatable part is coupled to the first link 300 and the second link 400 respectively; and a second magnetic body 140 disposed at a lateral end of the torso fastening part 100, wherein the first magnetic body 550 and second magnetic body 140 may be attracted to each other.

The first magnetic body 550 may be disposed at a position coincident with or at a position adjacent to the fifth point 530 of the rotatable part 500. The second magnetic body 140 may be disposed at an outer lateral end extending laterally from the torso fastening part 100, and may be disposed at a position extending from the torso fastening part 100 to the fixed link 200.

The first magnetic body 550 and second magnetic body 140 may be attracted to each other due to magnetism. When no external force is applied, the rotatable part 500 may be fixedly coupled to the torso fastening part 100 by the magnetic force between the first magnetic body 550 and the second magnetic body 140, as shown by the alternate long and short dash line of FIG. 6.

Accordingly, the combined structure of a wearable apparatus is maintained in a folded state when not worn by the wearer, thereby facilitating storage and transportation.

The upper arm module 700 may be applied with a rotational torque that rotates the upper arm module 700 upwardly with respect to the connecting part 600, and the fifth point 530 of the rotatable part 500 coupled with the connecting part 600 may be disposed at a position behind an intersection of the first link 300 and the second link 400.

As described above, the rotational torque that rotates the upper arm module 700 upwardly with respect to the connecting part 600 may be generated in the upper arm module 700, and a reaction thereagainst may be supported at the torso support through the connecting part 600.

In particular, between the fifth point 530 of the rotatable part 500 coupled with the connecting part 600, and the intersection of the first link 300 and the second link 400 that is the ICR 540 of the rotatable part 500, an offset spaced apart in the forward and backward direction may occur. In particular, since the fifth point 530 is disposed at a position behind the ICR 540 of the rotatable part 500, when the rotational torque is generated in the upper arm module 700, a force by which the rotatable part 500 is rotated forward about the ICR 540 may be generated.

Accordingly, without a separate harness or strap, the rotatable part 500 or the connecting part 600 is brought in close contact with the wearer's body and wearer's shoulder to follow the internal rotation and external rotation of the shoulder.

FIGS. 8 and 9 show the movement of the first link 300 and the second link 400 according to the rotation thereof at the first point 210 to the fourth point 520. In particular, the first link 300 and the second link 400 form a trajectory such as the following equation.

$$\vec{L}_1 + \vec{L}_2 = \vec{L}_4 + \vec{L}_3$$

$$\begin{bmatrix} \ell_1 \\ 0 \end{bmatrix} + \begin{bmatrix} \cos\theta_2 & -\sin\theta_2 \\ \sin\theta_2 & \cos\theta_2 \end{bmatrix} \begin{bmatrix} \ell_2 \\ 0 \end{bmatrix} = \begin{bmatrix} \cos\theta_4 & -\sin\theta_4 \\ \sin\theta_4 & \cos\theta_4 \end{bmatrix} \begin{bmatrix} \ell_4 \\ 0 \end{bmatrix} + \begin{bmatrix} \cos\theta_3 & -\sin\theta_3 \\ \sin\theta_3 & \cos\theta_3 \end{bmatrix} \begin{bmatrix} \ell_3 \\ 0 \end{bmatrix}$$

Accordingly, as the first link 300 and the second link 400 are rotated about the fixed link 200 fixed to the wearer as a fixed point, the third point 510 and the fourth point 520 of the rotatable part 500 are determined, and thus, a trajectory along which the fifth point 530 is moved is formed.

Figure 11:
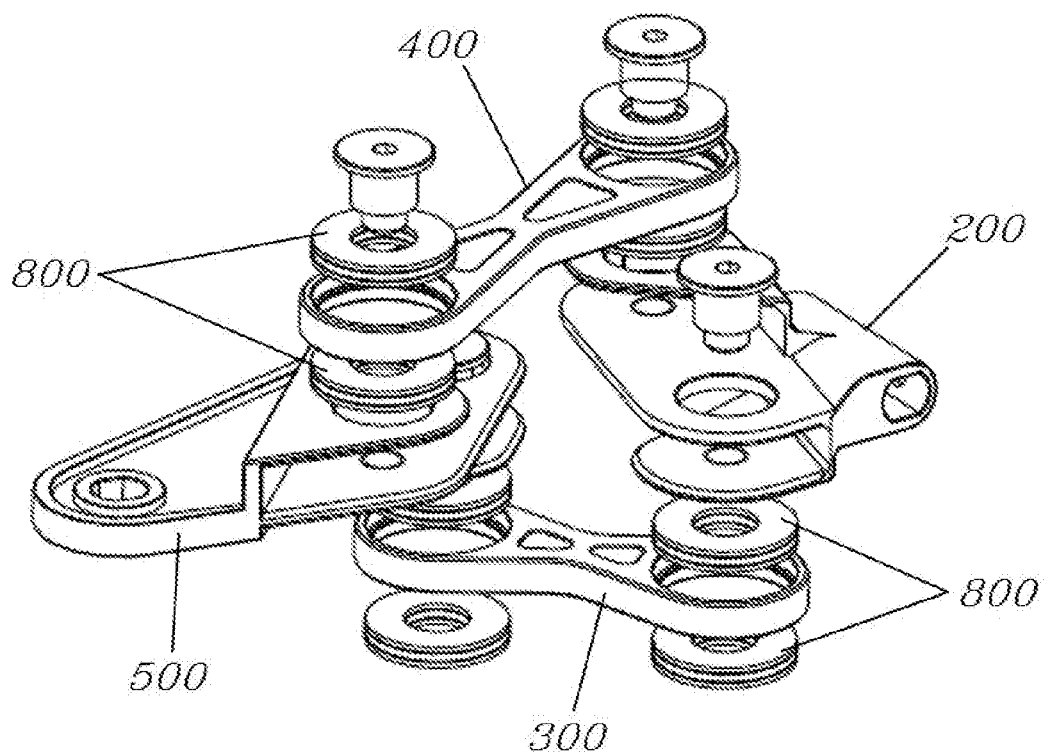
FIG. 11 is an exploded perspective view showing the first link and the second link included in the combined structure of a wearable apparatus according to an embodiment of the present disclosure.

FIG. 11 is an exploded perspective view showing the first link 300 and the second link 400 included in the combined structure of a wearable apparatus according to an embodiment of the present disclosure.

With further reference to FIG. 11, the first link 300 or the second link 400 may be coupled to the fixed link 200 or the rotatable part 500 through a thrust bearing 800, and may extend on planes parallel to each other while being vertically spaced from each other.

In other words, the first link 300 and the second link 400 are respectively coupled to the fixed link 200 and the rotatable part 500 to be vertically spaced from each other, and may include the bearings 800 to be rotatably coupled to the first point 210, the second point 220, the third point 510, and the fourth point 520, which are junction points.

In particular, the bearing 800 may be a thrust bearing 800 or an axial bearing 800. Thus, the thrust force acting in the direction of the rotation axis can be supported.

Referring again to FIGS. 1 and 2, the torso fastening part 100 may be disposed at a wearer's back side, and may include: an upper plate 110 disposed at an upper portion of the torso fastening part 100 to be brought in contact with the wearer's back side; a lower plate 130 disposed at a lower portion of the torso fastening part to be brought in contact with the wearer's back side; and a rear side link 120 extending in the vertical direction to connect the upper plate 110 and the lower plate 130 together.

In particular, the upper plate 110 may be fastened to the wearer's back side at a position higher than the wearer's shoulder, and the fixed link 200 may be disposed at a position above the wearer's shoulder by extending forward from a position where the upper plate 110 is laterally extended.

The upper plate 110 may be positioned behind the wearer's cervical vertebrae to be disposed above the wearer's shoulder, thereby being supported by being brought in contact with the wearer's neck. The fixed link 200 may be disposed at a position above the wearer's shoulder by extending forward while extending outer laterally from the upper plate 110.

Figure 12:
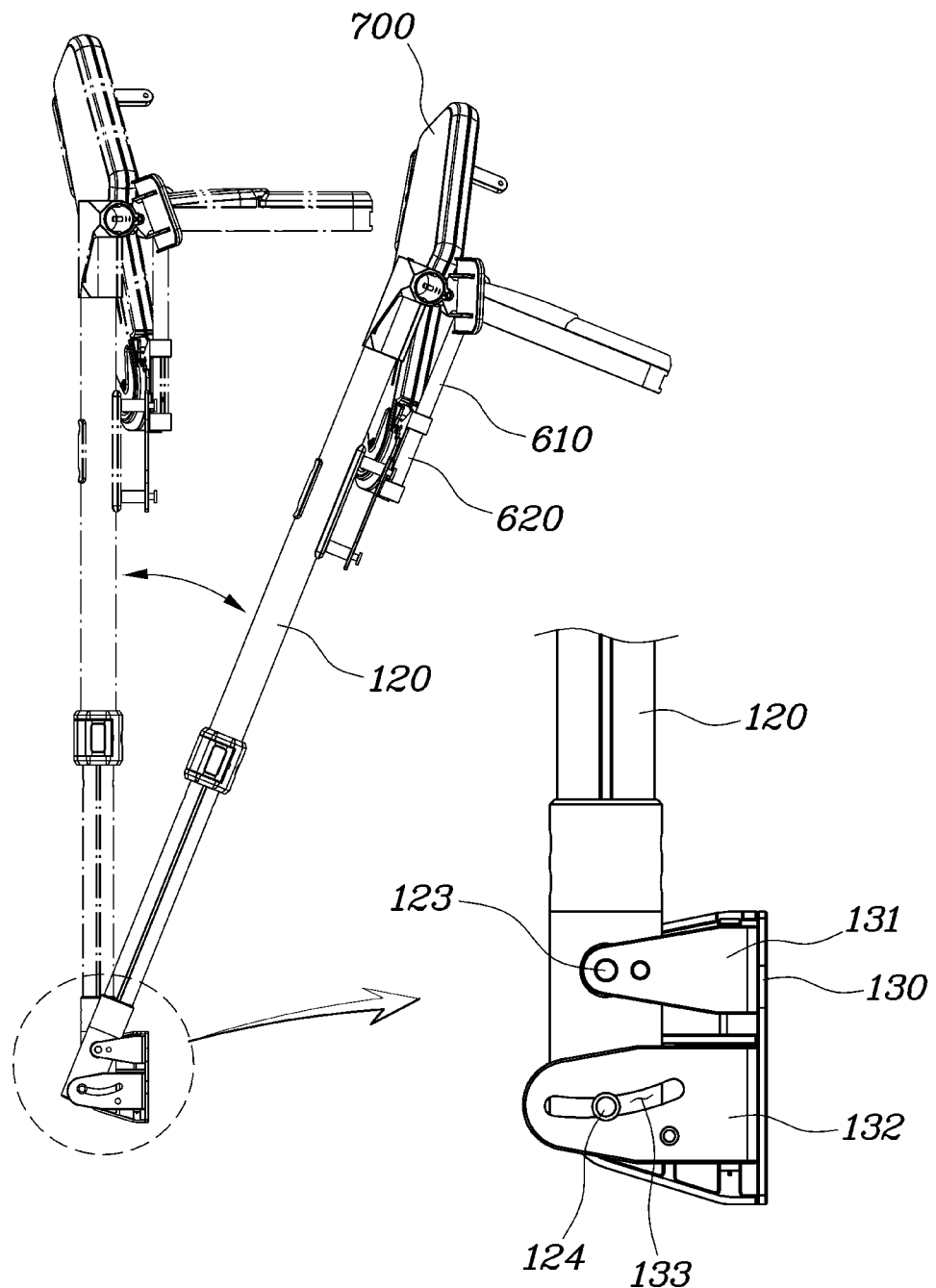
FIG. 12 is a view showing a forward and backward rotation structure of the combined structure of a wearable apparatus according to an embodiment of the present disclosure.

FIG. 12 is a view showing a forward and backward rotation structure of the combined structure of a wearable apparatus according to an embodiment of the present disclosure.

With further reference to FIG. 12, the lower plate 130 may be fastened to the wearer's back side at a position corresponding to a wearer's pelvis, and the lower plate 130 may be coupled to the rear side link 120 to be rotatable forward or backward.

In particular, the lower plate 130 may be provided with a first coupling portion 131 and a second coupling portion 132 protrudingly extending from positions vertically spaced apart from each other, and the rear side link 120 may be coupled to the first coupling portion 131 and the second coupling portion 132, wherein the first coupling portion 131 may be rotatably coupled to the rear side link 120, and the second coupling portion 132 may be slidably coupled to the rear side link 120.

The first coupling portion 131 may be rotatably coupled to the rear side link by a hinge coupling 123 between the lower plate 130 and the rear side link 120.

The second coupling portion 132 may be provided at a position downwardly spaced apart from the first coupling portion 131. The second coupling portion 132 may be formed with a sliding groove 133 at the lower plate 130, and the rear side link 120 may be formed with a sliding protrusion 124 sliding while being inserted in the sliding groove 133, so that the sliding protrusion 124 may slide while being inserted in the sliding groove 133 by the rotation at the first coupling portion 131.

Accordingly, it is possible to naturally simulate the motion of bending the waist forward or straightening the back backward.

Figure 13:
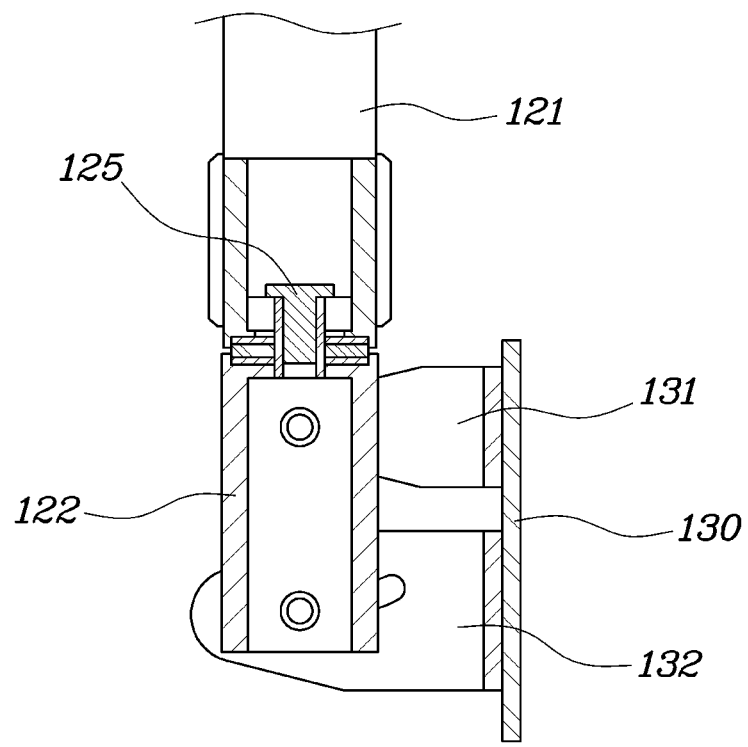
FIGS. 13 and 14 are views showing a lateral rotation structure of the combined structure of a wearable apparatus according to an embodiment of the present disclosure.
Figure 14:
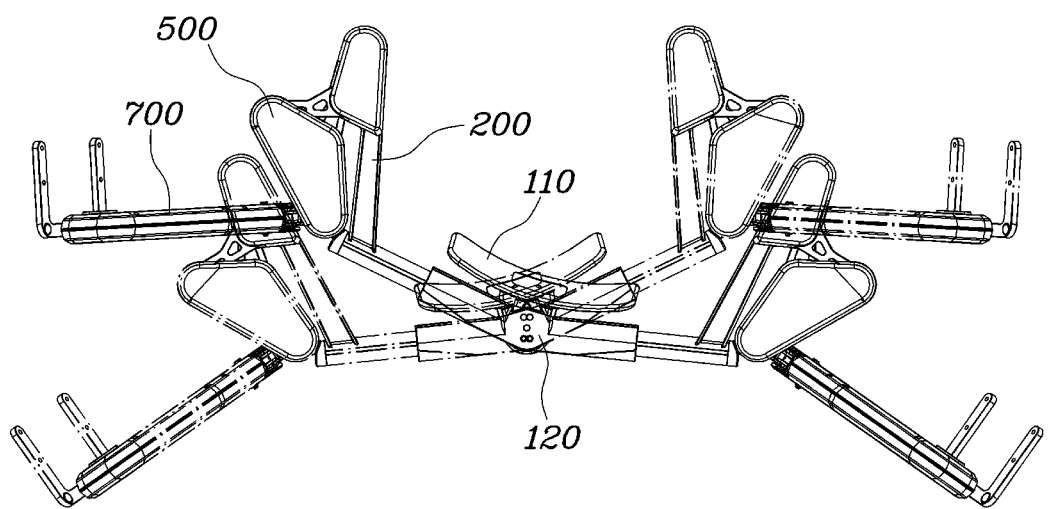

FIGS. 13 and 14 are views showing a lateral rotation structure of the combined structure of a wearable apparatus according to an embodiment of the present disclosure.

With further reference to FIGS. 13 and 14, the rear side link 120 may be rotatably coupled to the upper plate 110 or the lower plate 130 about an extended longitudinal direction as a rotation axis.

Accordingly, it is possible to simulate the rotational motion of the wearer's upper body in the Yaw direction.

As an embodiment, the rear side link 120 may be integrally rotated along with the upper plate 110 about a Yaw rotation axis which is a rotation axis parallel to the extended longitudinal direction of the rear side link 120. On the contrary, the rear side link 120 may be coupled to the lower plate 130 to be rotatable about a Yaw rotation axis which is a rotation axis parallel to the lower plate.

In particular, as shown in FIG. 13, the rear side link 120 may be constituted by an upper link 121 and a lower link 122 coupled to each other through a hinge joint 125 to be mutually rotatable about the Yaw rotation axis, wherein the upper link 121 may be disposed at an upper portion to be coupled to the upper plate 110, and the lower link 122 may be coupled to the lower plate 130 at a position under the upper link 121 to be rotatable along with the upper link 121 about the Yaw rotation axis. Accordingly, the wearer can rotate the torso based on the lumbar spine.

Although a preferred embodiment of the present disclosure has been described for illustrative purposes, those skilled in the art will appreciate that various modifications, additions and substitutions are possible, without departing from the scope and spirit of the disclosure as disclosed in the accompanying claims.

What is claimed is:

1. A combined structure of a wearable apparatus, the combined structure comprising:
 a torso fastening part configured to be fixedly fastened to a wearer's torso;
 a fixed link extending from the torso fastening part to a position above a wearer's shoulder;
 a first link and a second link being respectively coupled to the fixed link to be laterally rotatable, and crossing each other while being vertically spaced apart from each other;
 a rotatable part disposed at a position above the wearer's shoulder, and coupled to the first link and the second link to be laterally rotatable;
 a connecting part coupled to the rotatable part to extend downward from the rotatable part; and
 an upper arm module coupled to be rotatable upward or downward about the connecting part while an end thereof is coupled to the connecting part at a position corresponding to an upper end portion of a wearer's upper arm, and configured to be fastened to the wearer's upper arm and extended in a longitudinal direction of the wearer's upper arm,
 wherein the first link and the second link are respectively coupled to the rotatable part and the fixed link to form a four-bar linkage structure, and
 wherein the rotatable part coupled to the first link and the second link to be laterally rotatable is configured to rotate about an instantaneous center of rotation (ICR) formed at an intersection of the first link and the second link, the ICR configured to move along a semicircular path with only a single degree of freedom.

2. The combined structure of claim 1, wherein the torso fastening part is configured to be disposed at a wearer's back side, and includes:
 an upper plate disposed at an upper portion of the torso fastening part to be brought in contact with the wearer's back side;
 a lower plate disposed at a lower portion of the torso fastening part to be brought in contact with the wearer's back side; and
 a rear side link extending in a vertical direction to connect the upper plate and the lower plate together.

3. The combined structure of claim 2, wherein the lower plate is configured to be fastened to the wearer's back side at a position corresponding to a wearer's pelvis, and the lower plate is coupled to the rear side link to be rotatable forward or backward.

4. The combined structure of claim 3, wherein the lower plate is provided with a first coupling portion and a second coupling portion protrudingly extending from positions vertically spaced apart from each other, and
 the rear side link is coupled to the first coupling portion and the second coupling portion,
 wherein the first coupling portion is rotatably coupled to the rear side link, and the second coupling portion is slidably coupled to the rear side link.

5. The combined structure of claim 2, wherein the rear side link is rotatably coupled to the upper plate or the lower plate about an extended longitudinal direction thereof as a rotation axis.

6. The combined structure of claim 2, wherein the upper plate is configured to be fastened to the wearer's back side at a position higher than the wearer's shoulder, and the fixed link is disposed at a position above the wearer's shoulder by extending forward from a position where the upper plate is laterally extended.

7. The combined structure of claim 1, wherein the rotatable part is in a form of a plate extending parallel to a ground, is rotatably coupled to the first link and the second link respectively at a third point and a fourth point spaced apart from each other, and is coupled to the connecting part at a fifth point spaced apart from the third point and the fourth point.

8. The combined structure of claim 7, wherein the upper arm module is applied with a rotational torque that rotates the upper arm module upwardly with respect to the connecting part, and the fifth point of the rotatable part coupled with the connecting part is disposed at a position behind the intersection of the first link and the second link.

9. The combined structure of claim 1, wherein the fixed link extends forward from the torso fastening part to be disposed at a position above the wearer's shoulder, and is rotatably coupled to the first link and the second link respectively at a first point and a second point spaced apart from each other.

10. The combined structure of claim 1, wherein the first link or the second link is coupled to the fixed link or the rotatable part through a thrust bearing, and extends on planes parallel to each other while being vertically spaced from each other.

11. The combined structure of claim 1, further comprising:
   a first magnetic body disposed at an end of the rotatable part spaced apart from positions where the rotatable part is coupled to the first link and the second link; and
   a second magnetic body disposed at a lateral end of the torso fastening part,
   wherein the first magnetic body and second magnetic body are attracted to each other.

12. The combined structure of claim 1, wherein the upper arm module is configured to be disposed at an outer side of the wearer's upper arm, and includes a support that is configured to support the wearer's upper arm from a lower portion of the wearer's upper arm by extending toward an inner side of the wearer's upper arm along the lower portion of the wearer's upper arm.

\* \* \* \* \*